United States Patent
Snyder et al.

(10) Patent No.: US 7,090,888 B2
(45) Date of Patent: Aug. 15, 2006

(54) SUSTAINED RELEASE OPHTHALMOLOGICAL DEVICE AND METHOD OF MAKING AND USING THE SAME

(76) Inventors: Michael E. Snyder, 8561 Chaucer Pl., Montgomery, OH (US) 45249; Eric M. Dobrusin, 4225 Sandy La., Bloomfield Hills, MI (US) 48301

( * ) Notice: Subject to any disclaimer, the term of this patent is extended or adjusted under 35 U.S.C. 154(b) by 135 days.

(21) Appl. No.: 10/346,671

(22) Filed: Jan. 17, 2003

(65) Prior Publication Data
US 2003/0149479 A1 Aug. 7, 2003

Related U.S. Application Data

(60) Provisional application No. 60/397,698, filed on Jul. 22, 2002, provisional application No. 60/349,465, filed on Jan. 18, 2002.

(51) Int. Cl.
- B05D 7/02 (2006.01)
- B05D 7/00 (2006.01)
- A61F 2/14 (2006.01)
- A61L 27/28 (2006.01)
- A61L 27/40 (2006.01)

(52) U.S. Cl. ............... 427/2.21; 427/2.14; 427/2.24; 427/2.31; 427/162; 427/261; 623/6.42; 623/901

(58) Field of Classification Search ............ 427/2.14, 427/2.21, 2.24, 2.28, 2.31, 162, 164, 256, 427/258, 261, 402, 407.1; 623/4.1, 5.12, 623/6.16, 6.39, 6.42, 6.43, 6.62, 6.57, 901, 623/6.55

See application file for complete search history.

(56) References Cited

U.S. PATENT DOCUMENTS

| | | | |
|---|---|---|---|
| 4,853,224 A | 8/1989 | Wong | |
| 5,273,751 A | 12/1993 | Dubroff | |
| 5,375,611 A | 12/1994 | Lindqvist et al. | |
| 5,401,880 A | 3/1995 | Clark et al. | |
| 5,554,187 A | 9/1996 | Rizzo, III | |
| 5,569,463 A | 10/1996 | Helmus et al. | |
| 5,616,122 A | 4/1997 | Lam et al. | |
| 5,624,704 A | 4/1997 | Darouiche et al. | |
| 5,743,274 A | 4/1998 | Peyman | |
| 5,820,917 A * | 10/1998 | Tuch | 427/2.1 |

(Continued)

FOREIGN PATENT DOCUMENTS

EP 0544948 A1 6/1993

(Continued)

OTHER PUBLICATIONS

Pandey et al., Intracapsular ring sustained 5-fluorouracil delivery system for the prevention of posterior capsule opacification in rabbits: a histological study, J Cataract Refract Surg Jan. 28, 2002 (1): 139-48.

(Continued)

*Primary Examiner*—Timothy Meeks
*Assistant Examiner*—Wesley D. Markham
(74) *Attorney, Agent, or Firm*—Dobrusin & Thennisch PC (57) ABSTRACT

A method of making an ophthalmological implant by applying a layer of pharmaceutical agent and an overlying layer of a bioerodible material, a biodegradable material, a bioavailable material or a mixture thereof, the overlying layer having variable thickness and being dimensioned for prolonged release of the pharmaceutical agent from the implant as the overlying layer degrades.

4 Claims, 6 Drawing Sheets

U.S. PATENT DOCUMENTS

| | | | |
|---|---|---|---|
| 5,843,184 A | 12/1998 | Cionni | |
| 5,843,186 A | 12/1998 | Christ | |
| 5,853,760 A * | 12/1998 | Cremer | 424/484 |
| 5,876,438 A | 3/1999 | Kelleher et al. | |
| 5,902,283 A | 5/1999 | Darouiche et al. | |
| 5,980,928 A | 11/1999 | Terry | |
| 6,162,487 A | 12/2000 | Darouiche | |
| 6,206,916 B1 * | 3/2001 | Furst | 623/1.46 |
| 6,322,592 B1 | 11/2001 | Lucas et al. | |
| 6,352,542 B1 | 3/2002 | Snyder | |
| 2001/0004708 A1* | 6/2001 | Nagai | 623/4.1 |
| 2002/0099438 A1* | 7/2002 | Furst | 623/1.16 |

FOREIGN PATENT DOCUMENTS

| | | |
|---|---|---|
| KR | 2001-018344 A * | 3/2001 |
| WO | WO 00/62760 | 10/2000 |
| WO | WO 01/32140 | 5/2001 |
| WO | WO 02/100318 | 12/2002 |
| WO | WO 03/061625 | 7/2003 |

OTHER PUBLICATIONS

Shi W et al., Prolongation of corneal allograft survival in mice with a cyclosporine drug delivery system implant, Chung Hua Yen Ko Tsa Chih Aug. 38, 2002 (8): 502-5.

Mantripragada, S., A lipid based depot (DepoFoam technology) for sustained release drug delivery, Prog Lipid Res Sep. 2002 41 (5) 392-406.

Das et al., Effect of vancomycin on Staphylococcus epidermidis adherence to poly(methyl methacrylate) intraocular lenses, J Cataract Refract Surg Apr. 28, 2002 (4): 703-8.

Cheng et al., Treatment or prevention of herpes simplex virus retinitis withintravitreally injectable crystalline 1-0-hexadecylpropanediol-3-phospho-ganciclovir, Invest Ophthalmol Vic Sci Feb. 2002; 43 (2): 515-21.

Herrero-Vanrell et al., Biodegradable microspheres for vitreoretinal drug delivery, Adv Drug Deliv Rev Oct. 31, 2001; 52 (1): 5-16.

Herrero-Vanrell et al., Biodegradable PLGA microspheres loaded with ganciclovir for intraocular administration. Encapsulation technique, in vitro release profiles, and sterilization process, Pharm Res Oct 2002; 17 (10): 1323-8.

Jaffe et al., Fluocinolone acetonide sustained drug delivery device to treat severe uveitis, Ophthalmology Nov 2000; 107 (11):2024-33.

Jaffe et al., Safety and pharmacokinetics of an intraocular fluocinolone acetonide sustained delivery device, Invest Ophthalmol Vis Sci Oct 2002; 41 (11); 3569-75.

Kunou et al., Long-term sustained release of ganciclovir from biodegradable scleral implant for the treatment of cytomegalovirus retinitis, J Control Release Aug. 10, 2000; 68(2): 263-71.

Einmahl et al., Concomitant and controlled release of dexamethasone and 5-fluorouracil from poly(ortho ester), Int J Pharm 1999 Aug 20; 185(2): 189-98.

Tetz et al., Inhibition of posterior capsule opacification by an intraocular-lens-bound sustained drug delivery system: an experimental animal study and literature review, J Cataract Surg Oct 1996; 22 (8): 1070-9.

Rabowsky et al., The use of bioerodible polymers and daunorubicin in glaucoma filtration surgery, Ophthalmology May 1996; 103 (5): 800-7.

Nishi et al., Effect of intraocular sustained release of indomethacin on postoperative inflammation and posterior capsule opacification, J Cataract Refract Surg 1996; 22 Supp. 1: 806-10.

Chetoni et al., Ocular mini-Tablets for controlled release of timolol: evaluation in rabbits, J Ocul Pharmacol Ther 1996 Fall; 12 (3): 245-52.

Kiremitci-Gumusderelioglu et al., A novel MMC-loaded pHEMA drainage device for the treatment of glaucoma: in vitro and in vivo studies, J Biomater Sci Polym Ed 1996; 7 (1): 857-69.

Borhani et al., Suppression of experiemental proliferative vitreoretinopathy by sustained intraocular delivery of 5-FU, Int Ophthalmol 1995; 19 (1): 43-9.

Joshi A., Microparticulates for ophthalmic drug delivery, J Ocul Pharmacol 1994 Spring; 10(1): 29-45.

Rahimy et al., Polysulfone capillary fiber for intraocular drug delivery: in vitro and in vivo evaluations, J Drug Target 1994; 2 (4): 289-98.

Chang DF et al., Two Clinical trials of an intraocular steriod delivery system for cataract surgery, Trans AM Ophthalmol Soc. 1999; 97: 261-74; discussion 274-9.

DuBosar, Ryan, Intraocular steriod delivery system completes FDA phase 2 trial; New drug delivery system could make postop cataract managment easier and more efficient, Ocular Surgery News, a SLACK Incorporated newspaper, Nov. 1, 1997.

Chang, David F., An Intraocular Steriod Delivery System for Cataract Surgery, British Journal of Ophthalmology, Mar. 9, 2001.

* cited by examiner

SUSTAINED RELEASE OPHTHALMOLOGICAL DEVICE AND METHOD OF MAKING AND USING THE SAME

CLAIM OF BENEFIT OF FILING DATE

The present application claims the benefit of the filing date of U.S. Provisional Application Nos. 60/349,465, filed Jan. 18, 2002, and 60/397,698, filed Jul. 22, 2002, the contents of which are hereby incorporated by reference for all purposes.

TECHNICAL FIELD

The present invention relates to ophthalmologic implants and more particularly to implants that incorporate a sustained release pharmaceutical agent, such as a steroid, an antibiotic, an anti-inflammatory agent, antiglaucomatous, or a combination thereof.

BACKGROUND OF THE INVENTION

Currently available delivery systems for intraocular therapeutics are generally limited to 1) drops, which carry issues of expense, inconvenience, patient noncompliance (by overuse, underuse, or inappropriate frequency of use) as well as difficulty for delivery of the medications by certain patients (especially those with arthritic conditions who cannot manipulate the vials properly); 2) injections; and 3) bulky intravitreal implants placed within the vitreous cavity of the eye, requiring incisions in the eye and delicate manipulations of the vitreous gel .

There is a need to provide an efficient technique and device for introducing a pharmaceutical agent into the eye, particularly for sustained release following a surgical procedure. In another aspect, there is a need to provide an effective and convenient mechanism to deliver antibiotics, anti-inflammatory, antiglaucomatous, or other pharmaceuticals to the intraocular environment for therapeutic and prophylactic purposes, particularly following cataract or clear lens removal surgeries.

In yet another aspect, there is a need for an implant having applied thereto one or a plurality of sustained release pharmaceutical agents in a manner such that over time the active ingredient of the pharmaceutical agent (or agents) becomes bioavailable within an eye.

The following items may be relevant to the present invention and are hereby incorporated by reference herein for all purposes: U.S. Pat. Nos. 4,853,224; 5,273,751; 5,375,611; 5,401,880; 5,569,463; 5,616,122; 5,624,704; 5,843,184; 5,876,438; 5,902,283; 6,162,487; and 6,322,592.

SUMMARY OF THE INVENTION

The present invention provides an improved ophthalmologic implant (e.g., an endocapsular tension ring, an intraocular lens, or the like) that has attached thereto a pharmaceutical agent in a sustained release medium for implantation into a human eye. The implant may be fabricated in any of a number of different ways, but in a highly preferred embodiment, it includes a plurality of layers, at least one of which degrades, erodes or otherwise diminishes by becoming bioavailable over time to release an underlying layer including a pharmaceutical agent.

In one preferred embodiment, a pharmaceutical agent is dispersed in sustained release medium material that is coated over a surface of an implant, impregnated into a space within the implant or combination thereof.

In certain other preferred embodiments, the needs of the art are met by providing an improved ophthalmologic implant (e.g., an endocapsular tension ring an intraocular lens or the like) comprising:
  a) a filament or other implant member configured for insertion into an eye;
  b) a first layer including a pharmaceutical agent;
  c) a second layer overlying the first layer and including a bio-compatible sustained release medium material selected from a bioerodible material, a biodegradable material, a bioavailable material or a mixture thereof.

Among such particularly preferred embodiments, the present invention more specifically contemplates an ophthalmologic implant comprising:
  a) a filament configured for insertion into an eye;
  b) a first layer including a pharmaceutical agent;
  c) a second layer of variable thickness overlying the first layer and including a sustained release medium material selected from a bioerodible material, a biodegradable material, a bioavailable material or a mixture thereof, the second layer being dimensioned for prolonged release of the pharmaceutical agent from the ring as the second layer thickness becomes smaller.

In another alternative preferred aspect, the present invention contemplates a method for making an ophthalmologic implant comprising the steps of:
  a) providing a filament configured for insertion into an eye as an ophthalmologic implant selected from an endocapsular tension ring or an intraocular lens;
  b) attaching a first layer including a pharmaceutical agent to the filament; and
  c) attaching a second layer of variable thickness over the first layer, the second layer including a sustained release medium material selected from a bioerodible material, a biodegradable material, a bioavailable material or a mixture thereof, and the second layer being dimensioned for prolonged release of the pharmaceutical agent from the filament as the second layer becomes smaller.

The present invention contemplates not only methods of making ophthalmologic implants, but methods of implanting the implants into an eye (e.g., a human, a dog eye, horse eye or the like), therapies that employ the use of such an implant in an eye, as well as the implants themselves. The present invention affords numerous advantages including the elimination of a need for an implant recipient to receive prolonged post-operative therapy with topically applied pharmaceutical agents. In turn, this will help reduce post-operative prescription drug costs, and associated health care needs.

DETAILED DESCRIPTION OF THE INVENTION

In general, the ophthalmologic implants of the present invention will include at least one member, such as a filament, particularly one that is made of a biocompatible material that supports a pharmaceutical agent, and more preferably a pharmaceutical agent that is carried by a sustained release medium material, such as one selected from a bioerodible material, a biodegradable material, a bioavailable material or a mixture thereof.

The pharmaceutical agent herein may be a single agent, an admixture of agents, or multiple agents applied in simultaneous or serial coatings or layers. The pharmaceutical agent preferably is selected from an antibiotic, an anti-inflammatory, an antiglaucomatous, a steroid, or a combination thereof. By way of illustration (but without limitation to the employment of other unlisted agents), specific examples of pharmaceutical agents include 5-fluorouracil (5-FU), cyclosporine A (CsA), vancomycin, ganciclovir, fluocinolone acetonide, dexamethasone, daunorubicin, indomethacin, timolol, mitomycin-C, or mixtures thereof.

The pharmaceutical agent is preferably attached to an implant by applying a mixture that includes the pharmaceutical agent and a sustained release medium for functioning as a carrier or support, a barrier layer, or a combination thereof. Thus, the mixture may include a dispersion that includes a matrix and a pharmaceutical agent therein. It may alternatively or additional comprise layers, such a layer of a suitably carried pharmaceutical agent and a barrier layer over it.

Existing commercially available implants may be employed, or custom designed ones may be employed. In either case, the structure of the implant may be varied as desired for accommodating the pharmaceutical agent, such as by modifying the structure for increasing available surface area per unit volume. For example, in another preferred embodiment, a component of an implant (e.g., the filament) has wells, divots, pores, grooves, or other crevices for containing the pharmaceutical agent on one or more sides of the filament. The wells, divots, pores, grooves, or other crevices may vary in size, depth, or number along the length of the filament so as to correspond to a desired dosing regimen of the agent(s) over time. A variety of axial cross-sectional or longitudinal configurations could achieve similar results, including but not limited to spiraling, rifling, fluting, stippling, or dimpling. The surface of the implant may also be treated such as by surface roughening (e.g., mechanically, chemically or a combination thereof), a primer or other coating, or a combination thereof. The surface of the implant might be crosslinked with a pharmaceutical compound or moiety, or a polymer or oligomer containing the same.

In one embodiment, it is contemplated that the pharmaceutical agent is supported or carried by a porous structure. Such a structure may be made by producing a mixture that includes at least one porogenic agent, compacting or shaping the mixture to its desired form, and heating or otherwise treating (e.g., by solvent) the product obtained in such a way that the porogen is removed. At least one pharmaceutical agent may be incorporated in the pores where the porogenic agent used to be.

In another embodiment, the pharmaceutical agent may be applied in a first state and reacted or otherwise transformed to form a second state. For instance, an implant may be dipped in a pharmaceutical agent and then irradiated, heated or otherwise treated.

When the implants are coated, in accordance with any of the processing steps herein, they may be coated by a suitable coating technique, including (by way of example, without limitation) spraying, dipping, swabbing, brushing, rolling, curtain coating, doctor blading, vapor deposition or combinations thereof.

In yet another embodiment, it is also possible to place an implant in a mold and overmold the implant with a material including a pharmaceutical agent.

The implants, sustained release medium, a pharmaceutical agent, or a combination thereof may also include a suitable polymeric agent for increasing tack, for enhancing penetration or both. An example of a suitable additional agent is disclosed in U.S. Pat. No. 6,162,487, hereby incorporated by reference.

A highly preferred embodiment of the present invention is to employ an antibiotic as a pharmaceutical agent. However, the present invention is not limited to antibiotics. Thus, pharmaceutical agents for use in accordance with the present invention may be selected from antimicrobials, antithrombotic agents, antiseptics, antibiotics, anti-fungal agents, steroids, chelating agents, anticoagulants, or combinations thereof. Other pharmaceutical compounds may also be employed.

It may be the case that a pharmaceutical agent is coated onto an implant or is delivered to a matrix material in combination with an art-disclosed pharmaceutically acceptable carrier that may be the same as or different from the sustained release medium. Such carrier preferably is relatively inert relative to the pharmaceutical agent, and also is generally bio-compatible. Accordingly, it will be appreciated that the sustained release medium herein, any carrier, a pharmaceutical agent, or combination thereof may be solid, semi-solid, liquid, gel, amorphous solid, crystalline solid, freeze-dried, spray-dried, supercooled, or provided in any other suitable form.

It will be appreciated that the present invention is suitable for use or in connection with a number of different ophthalmologic implants, including but not limited to an endocapsular tension ring or an intraocular lens. It should be appreciated that any structure associated with the implant (e.g., a haptic, an endocapsular component or otherwise) may be varied as desired. For example, a suitable implant structure that is configured to be held within a capsular bag of an eye can be coated in accordance with the present invention, and may include an arc-shaped "J-loop", arc-shaped "C-loop", a complete circumferential support member, a partial circumferential support member, a plate (e.g., a plate haptic configuration), a radial support member, a pararadial support member, a tangential support member, a circumferential support member, or a combination thereof.

The gross shape of the implant is such so as to be readily placed within an eye. By way of example, an endocapsular tension ring is configured so as to be positioned within the fornix of the capsular bag, as is typical with the known standard endocapsular tension rings. The implants may be made of any suitable material, e.g., a plastic material such as poly(methylmethacrylate) or other acrylic, preferably for affording some flexibility with the gross structure of the implant.

Among the many alternative configurations of the present invention, examples of combinations contemplated by the invention include:

1) A member with a hollow core in which a pharmaceutical agent, sustained release pharmaceutical agent or medicinal material is impregnated into the core, pores or crevices on a surface of the member, or coated pharmaceutical agent could be pre-loaded (either by manufacture or postmanufacturing preparation) or placed intraoperatively. The aqueous material of the eye could percolate or flow through the cavity via openings at either ends, channels, grooves, fenestrations, or other openings between the central core and the outer wall.

2) A ring with a solid or hollow composition with one or more elements, grooves, or other modifications of the ring which affix or allow the fixation of a pharmaceutical agent, sustained release pharmaceutical agent or material impregnated with a pharmaceutical agent, whether in the form of a filament, aggregate, film, or other geometric or non-geometric configuration; or 3) A ring composed of pharmaceutical agent, sustained release pharmaceutical agent or biodegradable material impregnated pharmaceutical agent.

A ring as described above could be designed for fixation within the ciliary sulcus or pars plana of the eye either by passive means or suture fixation to the eye.

Turning in detail to a highly preferred embodiment of the present invention, a method is employed pursuant to which a pharmaceutical agent is applied to an implant and thereafter, the implant with the pharmaceutical agent thereon is coated continuously, intermittently, uniformly, non-uniformly, entirely or partially with a non-toxic, sustained release medium material, which would allow for sustained release of the pharmaceutical agent. A preferred common characteristic for the sustained release medium material (which may be a polymer, a starch or other suitable material), will diminish over time by contact with or exposure to enzymes, hydrolysis, surrounding tissue fluids, cells, or the like.

In a highly preferred embodiment, the sustained release medium material is provided as a barrier layer, such as one having a varying (e.g., tapering continuously, step-wise or a combination thereof) thickness along the length of the filament so that the pharmaceutical agent at different positions along the length of the ring would be released at different times, depending on the thickness of the layer at a particular point along the length of the implant. The thickness may vary in a tapering thickness from one end of the ring to the other, a sinusoidal thickness along the ring length, or in a step-wise variation in thickness. In such a stepwise variant, then length of each step may determine the dosing interval, while the thickness of the layer coating at any given step would determine when that aloquot of pharmaceutical agent would be released.

In another highly preferred embodiment, the pharmaceutical agent(s) may exist within an admixture of the sustained release medium material, perhaps in the form of liposomes or some other mechanism of micropackaging of the pharmaceutical agent(s). One or more admixtures containing one, two, or more pharmaceutical agents could be applied to the ring, either varying along the length or with serial, overlapping coatings, so as to vary the agent(s) and doses of the agent(s) per unit time over time.

In one embodiment, the ring filament is first coated over some or all of its outer surface with a pharmaceutical agent and then the bioerodable (or as discussed above a biodegradable or bioabsorbable material) is applied in a varying thickness over the pharmaceutical agent.

To illustrate, in one highly preferred embodiment, an implant member would be placed on a suitable surface, e.g., a substantially planar surface, and one or more pharmaceutically active agents would be sprayed, swabbed, brushed, vaporized, dipped or otherwise coated continuously, intermittently, uniformly or non-uniformly, entirely or partially onto the exposed surface of the filament and allowed to dry, polymerize, crystallize, or otherwise adhere or attach. The implant could be turned over, exposing the previously downfacing, protected surface. Another application of the same or other pharmaceutical agent(s) or admixture of agents would be similarly applied to the now upward, exposed surface and similarly allowed to dry, polymerize, crystallize, or otherwise adhere or attach. The filament could then be weighted at an end or otherwise drawn into a straight, hollow tube, effectually straightening out the ring-shaped native configuration of the filament. The sustained release medium material could then be applied in a uniform, tapered, or stepwise tapered fashion by either serial dipping, at varying locations along the length of the straightened complex, immersion with a varying time of immersion for varying portions along the length of the implant within a fluidic medium including the sustained release medium as to predicatably vary the thickness of the sustained release medium along the length of the implant. Alternatively, the tube could act as a mask so that the sustained release medium could be applied in varying thicknesses by varying the amount of the length of the implant exposed for varying duration of time while by being sprayed, swabbed, brushed, vaporized, sputtered, dipped or otherwise coated.

An another highly preferred embodiment, the implant could be coated, as described above, or otherwise, with one or more layers of one or more admixtures of a degradeable layer, such as a layer that includes a bioerodable agent and/or a pharmaceutical agent(s). For example, one or more initial coats of a sustained release medium may include pharmaceutical agent(s) with or without steroid, properties, while one or more subsequent outer coats of another admixture might include pharmaceutical agents with or without steroid antimicrobial properties. This type of configuration would have the effect of delivering antimicrobial and anti-inflammatory agents first, then eliminating the antimicrobial agent from the sustained release admixture once the window of vulnerability of infection has passed. As to certain pharmaceutical agents, one skilled in the art should recognize that there may be little risk to allowing a continued non-toxic dose release of antimicrobial agent to occur during the entire duration of planned time of release of the other pharmaceutical agent. In such a setting a single admixture applied either in one or more coats might suffice.

A practitioner skilled in the art will also recognize the potential benefits of adding other or additional pharmaceutical agents, depending on the nature of the recipient eye's other coexisting disease(s) and future as yet unknown applications of pharmaceutical agents which, may include other anti-infective, anti-ocular hypertensive anti-inflammatory, anti-angiogenesis, antiproliferative, anti-neoplastic, growth factors, stimulatory agents or, even vectors for introduction of gene therapy or gene modulating agents.

It will also be appreciated that some or all of the polymer coating may include a dispersion of a pharmaceutical agent. It is also possible using the invention described herein to design a therapy where two or more different pharmaceutic agents are incorporated in the sustained release medium material, the pharmaceutic agent layer or both. The quantities of each may be variable along the length of the filament. Thus it is possible that a first agent is incorporated for release over a first time period (e.g., during the first about 1 to about 8 days following implant) and a second or additional agent is incorporated for release over a different time period (e.g. during the about 1 to about 30 days following implant, or commencing after a certain period of time, such as after about 7 days).

By way of example, in one preferred embodiment of the invention, designed for following routine anterior segment eye surgery, the pharmaceutical agent delivery might occur along a schedule as follows:

1) Antimicrobial agent: Released to achieve at least microbiocidal levels in the eye fluids for at least 4–7 days at a non-toxic level to the native intraocular tissues.
2) Steroid agent: Released at gradually taper dosage over approximately 28–40 days.
3) Non-steroidal anti-inflammatory drug (NSAID): Released at gradually taper dosage over approximately 28–40 days.

Other agents may be desired in some cases or as newer pharmaceuticals become available.

The particular bio-compatible material for use as a sustained release medium may be selected as desired. Such material may be provided for securing onto an ophthalmologic implant in a form selected from a liquid, a powder, a gel, or a mixture thereof. Solid materials may be crystalline, amorphous, or a mixture thereof, either in their as provided state or in an intermediate or final state. The material may include or consist essentially of a small molecule, an oligomer, a polymer (organic, biological or a combination thereof), or combinations thereof. Preferably the material is of one or more pH levels that are compatible with an eye.

The specific material may vary. Examples of materials that may be employed for providing a sustained release include, without limitation, caprolactones (e.g., a polyactide-coglycolide-co-caprolactone (PGLC) polymer), multi-vesicular liposomes (e.g., with unilamellar vesicles, mutilamellar vesicles, neosomes, closely packed non-concentric vesicles (such as DEPOFOAM™), or combinations thereof), salts (e.g., an ammonium salt of 1-0-hexadecyl-propanediol-3-phospho-ganiclovir (HDP-P-GCV)), poly (lactic acid), poly (glycolic acid), copolymers of lactic and glycolic acids, poly (DL-lactide-co-glycolide) (PLGA) or blends of PLGA of different molecular weights, poly (orthoester), acrylic polymers, methacrylic polymers, poly (hydroxyethylmethacrylate), polysulfone or mixtures thereof. The present invention contemplates that the material employed may be one that is not listed herein and the omission from the above list should not be construed as limiting of the scope of the invention.

It is contemplated that a suitable material for delivering a pharmaceutical agent might include a material that releases the agent over time through or as a result of diffusion, chemical reaction, ion exchange, degradation or combination thereof.

The materials may comprise microspheres, microparticles, other vesicles, capillaries, combinations thereof, or other forms.

The amount of material, the method of application to an implant or both are selected so that any pharmaceutic that is carried with or by the material can be released continuously, in spaced intervals, or a combination thereof, over a predetermined period of time of at least one minute, at least an hour, at least a day, at least a week, at least a month, at least a year or longer. The bio-compatible material may be a pharmaceutical agent itself, or it may function as a support or carrier for the pharmaceutical agent.

The present invention may be used for delivery of any of a number of different applications. In one preferred embodiment, a method is contemplated pursuant to which a crystalline lens of the eye is removed (e.g., either by cataract surgery, clear lens removal surgery, or otherwise), and an implant (e.g., a tension ring) is placed into the fornix of the capsular bag, such as by use of an injector mechanism or by direct placement. The implant can stay within the capsular bag permanently without need for removal, and may share the contents of the capsular bag with an intraocular lens, an artificial iris prosthesis, or another intraocular prosthesis designed for intracapsular positioning.

For example, one method of the present invention contemplates including a step of placing of a suture length or other filament, carrying an ocular antihypertensive medication, in the subconjunctival space of a patient having glaucoma. Another method contemplates including a step of placing of a suture length or other filament, carrying cyclosporin or another agent in the subconjunctival space of an eye for treating dry eye. The present invention also contemplates applying an antibiotic or wound healing pharmaceutical agent to a suture for inserting anywhere in the body.

In yet another method, a ring carrying an antiglaucomatous medication is implanted within an eye.

In yet another method, such as in an instance when a capsular bag has been damaged and an implant can not be readily placed within the fornix, it is possible that a step is employed in which a passive fixation, suture fixation, or both, of the implant is performed within the ciliary sulcus of the eye.

The medicinal materials of the present invention may also be included on other surgical supplies for use in an eye, such as sutures or surgical instruments.

The implants of the present invention may be permanent or temporary. Accordingly, the methods herein also contemplate performing a subsequent removal, replacement, or both, of an implant. While it is typical that many of the implants herein will be employed for a single use and then disposed of, it is also possible that implants may be removed and re-used (including a possible step of re-treating the implant for adding more pharmaceutical agent. Removal and replacement of on implant on a periodic basis is thus contemplated, either at regular intervals of similar amounts of time or at different amounts of time.

Turning now to examples of different structural embodiments, reference is made to the drawings. Various other embodiments will be apparent as well from a review of the drawings, which are not intended as limiting. For example, in some drawings, it is illustrated that the outer layer is generally tapered. It need not be, but can be of constant cross section. For example, there can be different thicknesses of barrier layer, pharmaceutic agent layer, the implant or a combination thereof over discrete locations along the implant. Further, the respective consecutive doses need not be adjacent to one another but can be staggered over the length of the filament. The corners of the coatings that correspond to the respective doses that are depicted in the drawings herein may also be smooth curves. The implant may also be structured as a helical or with threads for varying its surface topography.

Figures 1, 2, 3, 4:
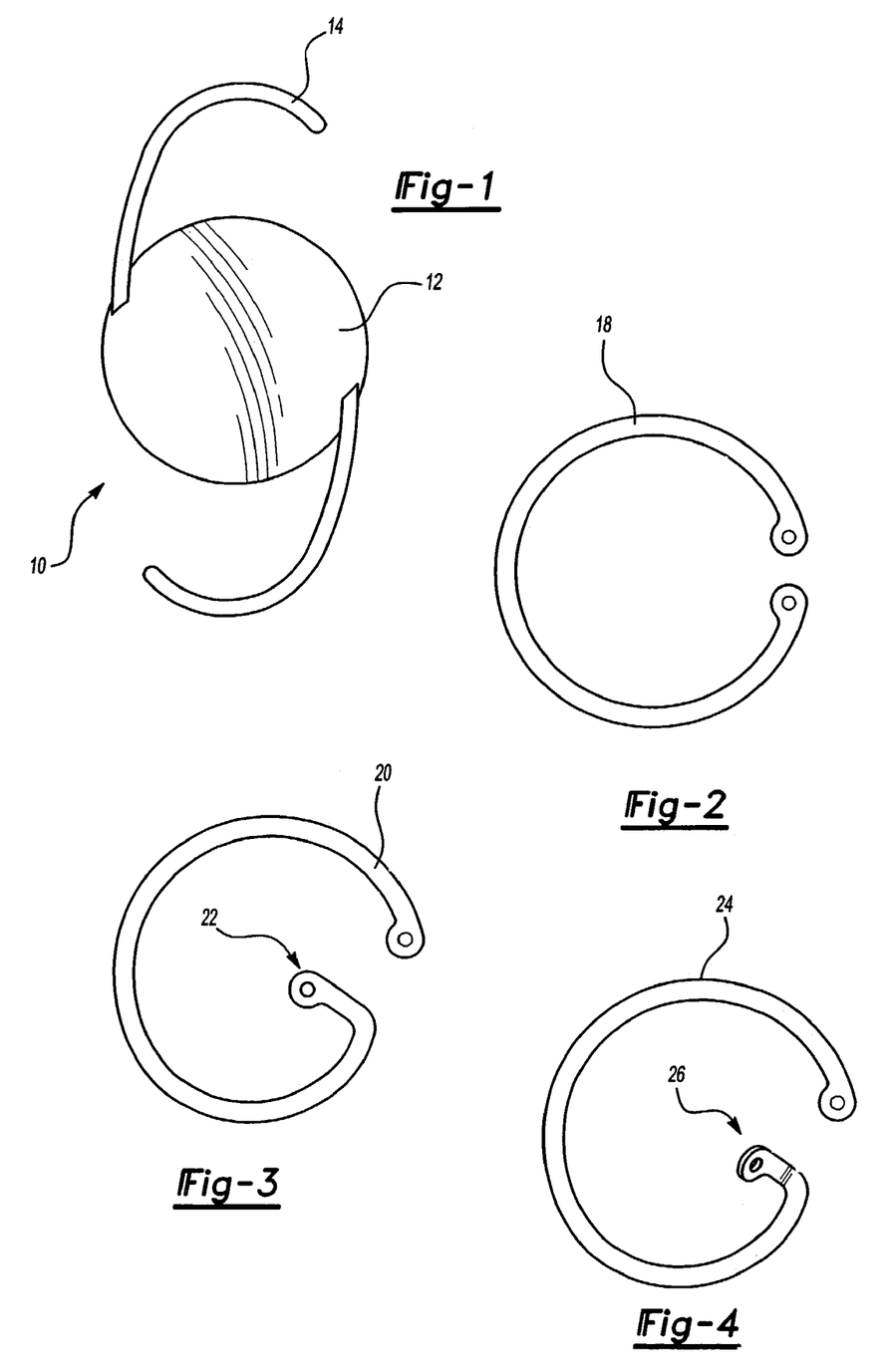
FIG. 1 illustrates a plan view of a general configuration of an intraocular lens.
FIGS. 2–4 illustrate plan views of various endocapsular tension ring devices that may be treated in accordance with the present invention.

FIG. 1 shows an intraocular lens (IOL) 10 that may be treated in accordance with the present invention. The IOL 10 includes a lens portion 12 and one or more haptics 14. Examples of various other IOL configurations can be gleaned from U.S. Pat. No. 6,352,542, and the art cited therein, hereby expressly incorporated by reference.

FIGS. 2–4 illustrate examples of a first endocapsular tension ring 18, a second endocapsular tension ring 20, and a third endocapsular tension ring 24, all including positioning holes at their ends. From FIG. 3, it is seen that there may be included a radially centrally extending portion 22 to help facilitate possible ring exchange when repeated or prolonged closing is desired. FIG. 4 includes a centrally extending end portion 26 that may be open or openable, so as to define an internal cavity into which additional doses of a pharmaceutical agent may be introduced subsequently.

Figure 5:
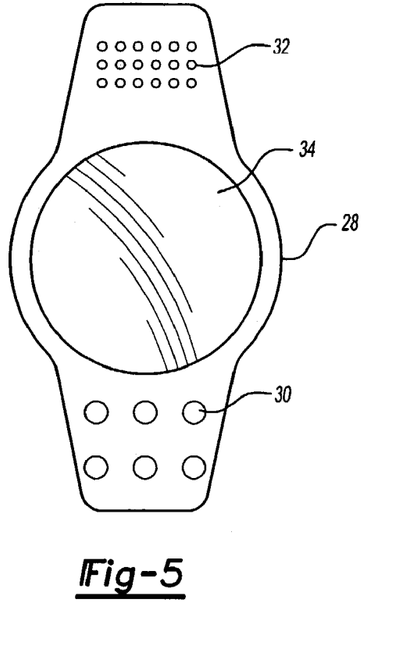
FIGS. 5–13 illustrate views showing how a sustained release medium may be employed on an implant.
Figure 6:
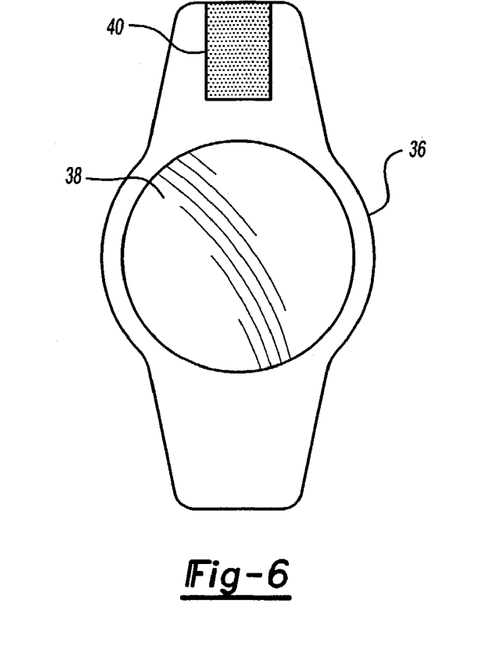

Additional alternative implant structures, without limitation, are shown in FIGS. 5 and 6, where there are depicted examples of plate haptic IOLs 28 and 36. More specifically, the IOL 28 of FIG. 5 includes a lens 34 and opposing plate end portions having perforations 30 and 32 therein. The perforations may be the same or different size and the same or different number on either side of the lens 34 for permitting access to a pharmaceutical agent.

FIG. 6 shows a variation of FIG. 5, in which one (or optionally both) of the plate portions adjoining lens 38 has a channel 40 or is otherwise adapted for receiving a pharmaceutical agent.

It will be realized that the embodiments of FIGS. 1–6 may be adapted in any suitable manner and may include any suitable structure for supporting a pharmaceutical agent, including those discussed herein.

By way of example, with reference to FIGS. 7–13, there are shown various structural alternatives for securing a pharmaceutical agent (e.g., supported pharmaceutical agent) to an implant.

Figure 7:
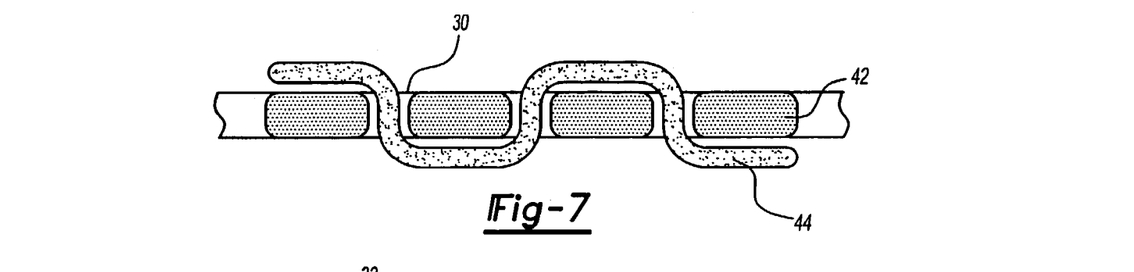

For example, in FIG. 7, a sectional view of FIG. 5, the pharmaceutical agent may be provided as a filament, ribbon, film, cord, or other member 44 that is woven through perforations 30 of a plate portion 42 of a haptic, such as the haptic of FIG. 5.

Figure 8:
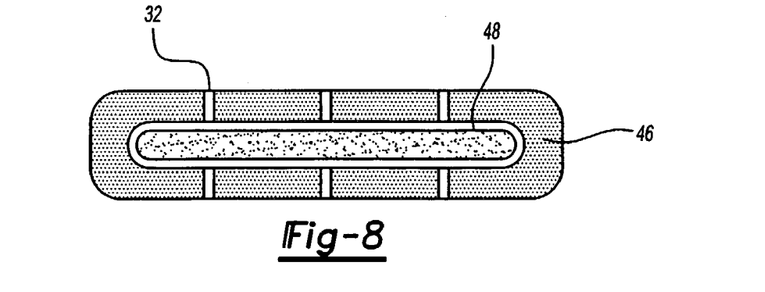

In FIG. 8, there is seen an approach where a plate portion 46 has a cavity for receiving a pharmaceutical agent 48. The plate portion is such that perforations 32 from one or more sides of the plate portion allow transport of the pharmaceutical agent through the plate portion.

It will be appreciated that the approaches of FIGS. 7 and 8 may be used in combination in a single implant, as in FIG. 5, or they may be used individually.

Figure 9:
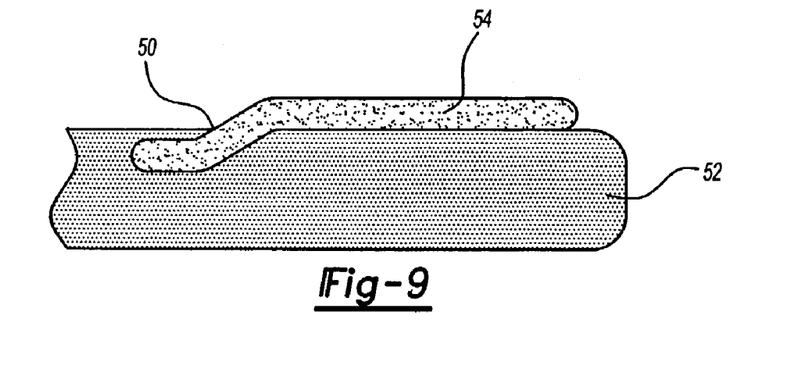

Turning to FIG. 9, there is shown a possible approach to carrying a pharmaceutical agent on an external portion of a plate haptic, such as the type of FIG. 6. In this embodiment, an aperture 50 may be defined in the plate portion 52 onto which a filament, ribbon, film, cord, or other member 54 may be inserted, coated, bonded or otherwise attached or affixed.

The embodiment of FIG. 9 likewise may be used alone or in combination with one or both of the embodiments of FIGS. 7 and 8.

Turning now to FIGS. 10–13, there are shown alternative approaches for treating a thin member, such as a haptic (e.g., wire or plate) an endocapsular tension ring or other structure for carrying a pharmaceutical agent.

Figure 10:
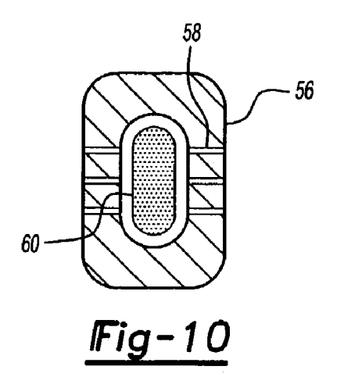

In FIG. 10, showing a view in cross-section, member 56 includes passages 58 in communication with a central passage into which a pharmaceutical agent 60 may be introduced.

Figure 11:
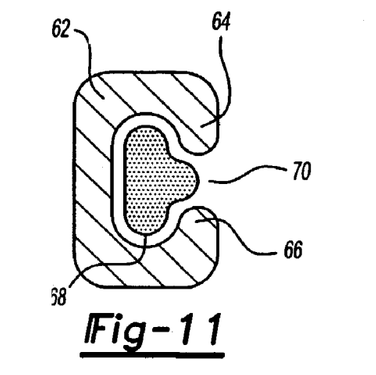

In FIG. 11, a member 62 includes opposing spaced ends 64 and 66 and an opening for receiving a pharmaceutical agent 68. The agent 68 is released through an opening 70 defined by the ends 64 and 66, which may be a hole, a channel or otherwise.

Figure 12:
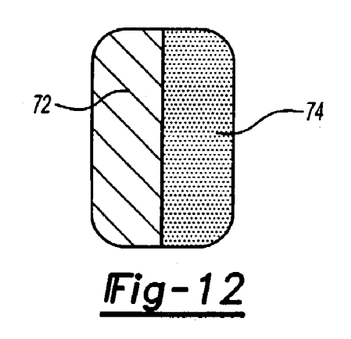

In FIG. 12, there is seen an approach wherein an implant is laminated to include a member 72 having a layer 74 with a pharmaceutical agent attached thereto.

Figure 13:
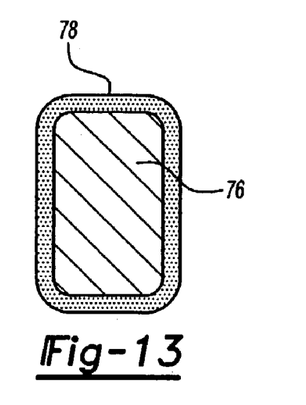

FIG. 13 shows yet another alternative, pursuant to which a member 76 is coated over at least a portion, if not substantially the entirety of its outer surface with a layer 78 including a pharmaceutical agent.

The embodiments illustrated in FIGS. 7–13 are not intended as limited to the employment of a pharmaceutical agent dispersed or otherwise carried in a matrix of a suitable pharmaceutical carrier. As the discussion of FIGS. 14–28 will demonstrate, and as discussed herein, other layers or combinations are possible.

For example, the various embodiments of FIGS. 14–28, illustrate the concepts discussed herein of employing a barrier layer that will diminish over time for exposing a thereby releasing pharmaceutical agent. The barrier layer may be smooth, or irregular (e.g., stepped, jagged, or otherwise) over some or all of its outer surface, inner surface or combination thereof. Preferably, the barrier layer overlies a layer of pharmaceutical agent, which in turn is disposed on or within an implant member, that effectively is a core of the device. The layer of pharmaceutical agent likewise may be smooth or irregular over some or all of its outer or inner surface, as may be the underlying implant member itself.

Figure 14:
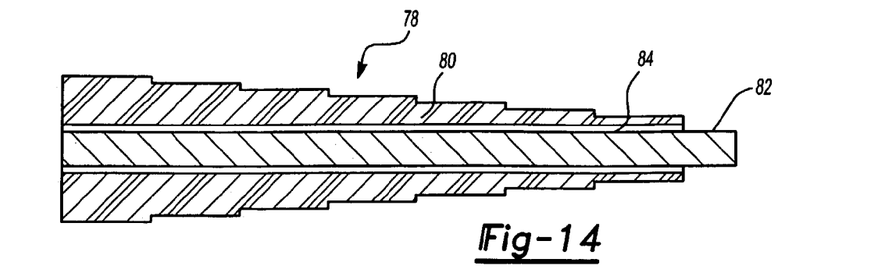
FIGS. 14–28 illustrate longitudinal cross-sectional views of various alternative structures in accordance with the present invention.

FIG. 14 illustrates a device 78 that has a variable sectional thickness stepped barrier layer 80, over an implant member 82, with a region 84 in which pharmaceutical agent is located.

Figure 15:
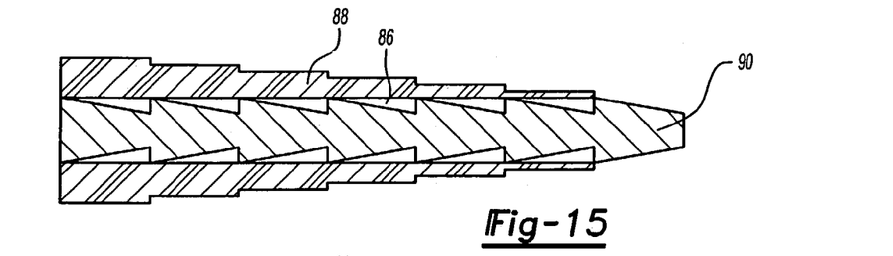

FIG. 15 shows a structure that has a region of pharmaceutical agent 86 generally beneath variable sectional thickness stepped barrier layer 88. The region 86 varies in thickness along the length and as a result of a notched or corrugated structure of an implant member 90 outer surface.

Figure 16:
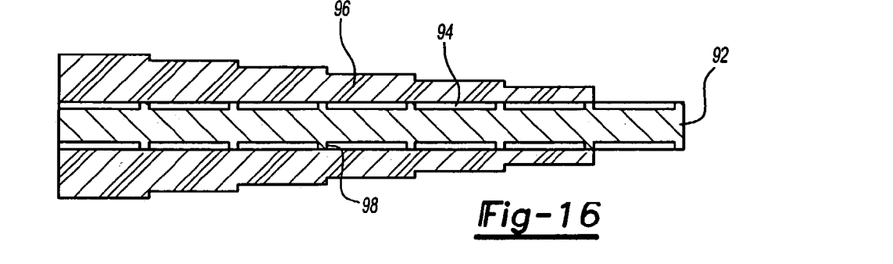

FIG. 16 shows an implant member 92 with overlying region 94 of pharmaceutical agent a variable sectional thickness stepped barrier layer 96. The member 92 further includes axially spaced flanged 98 for dividing the region 94 into subregions. The presence of subregions here, as in other embodiments disclosed (e.g., FIG. 15) is that a plurality of different pharmaceutical agents may be carried, each in a different subregion. Further, it is possible to delay the start of another dose by requiring the barrier layer to become eliminated.

Figure 17:
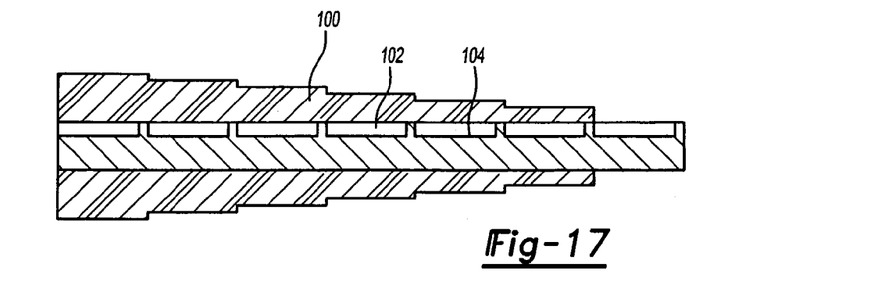
Figure 18:
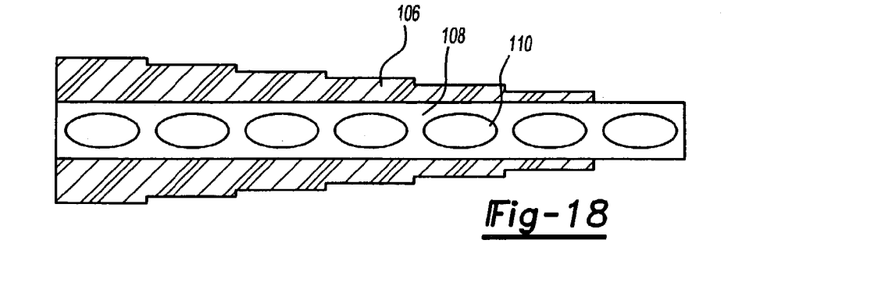

FIGS. 17 and 18 illustrate an alternative to FIG. 16 in which the subregions are further defined shaped wells. From a side view, as seen in FIG. 17, a barrier layer 100 may overlie pharmaceutical agent subregions 102 defined by a predetermined structure of an implant member 104. The top view of FIG. 18 illustrates an example of an implant member surface 106 that has walls 108 for defining a well 110. Each well may carry the same or a different pharmaceutical agent.

Structures for the implant members, shown in FIG. 17, may alternatively employ ribs along the length, such as axially spaced circumferential or partially circumferential ribs.

Figure 19:
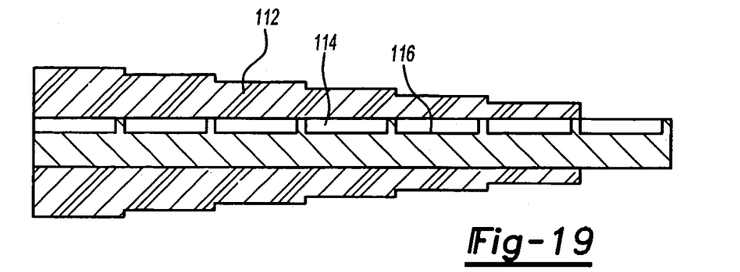
Figure 20:
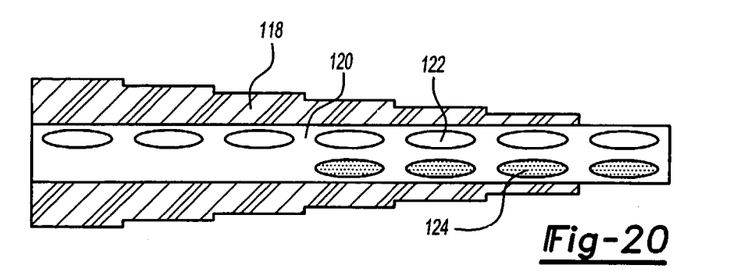

FIGS. 19 and 20 illustrate yet another alternative embodiment in which subregions are defined. As seen from a side view in FIG. 19, a barrier layer 112 overlies subregions 114 with a pharmaceutical agent, carried over an implant member 116. In the embodiment of FIG. 20, there is shown an option for further controlling dosing by providing beneath a barrier layer 118, an implant member 120 having first wells 122 and second wells 124. The first wells 122 may extend over a different length of the implant member 120, so that after a period of time only the pharmaceutical agent of the first wells is released.

Figure 21:
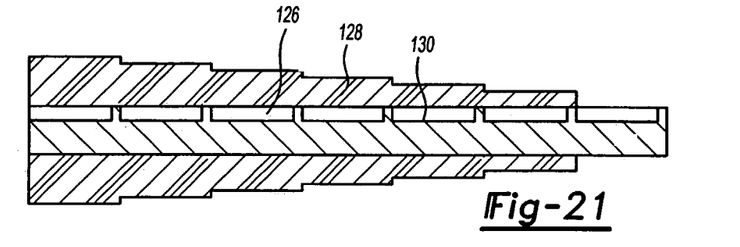
Figure 22:
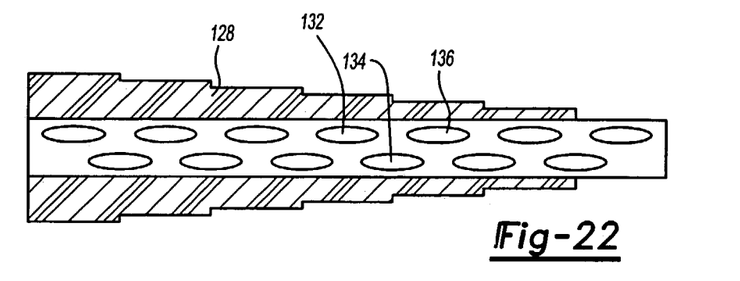

The embodiments of FIGS. 21 and 22 illustrate yet another alternative employing a pharmaceutical agent region 126, a barrier layer 128 and implant member 130. In this aspect, at least first well 132, second well 134 and third well 136 are staggered in partially overlapping relation to each other where the second well spans at least the length between the first well 132 and third well 136, for helping to assure more continuous and less episodic release of the pharmaceutical agent.

Figure 23:
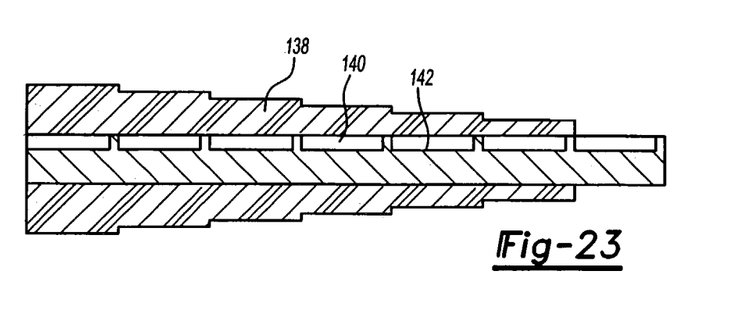
Figure 24:
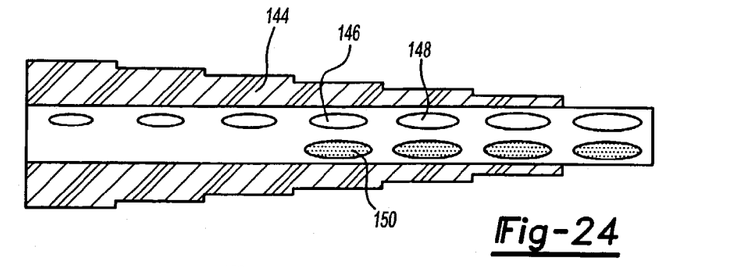

The embodiments of FIGS. 23 and 24 show yet another alternative embodiment, in which well sizes are varied for receiving different volumes of pharmaceutical agent. Thus a barrier layer 138 over a pharmaceutical agent region 140 can be configured on an implant member 142 so that (as seen from the top view of FIG. 24), a wall 144 defines first, second and optionally third wells 146, 148 and 150.

Instead of varying the length of the well, it is also possible to vary its height. Moreover, as appreciated, the barrier layer of each of the embodiments shown need not be stepped or irregular, but may be smooth and continuous of constant thickness, sloping thickness.

Figure 25:
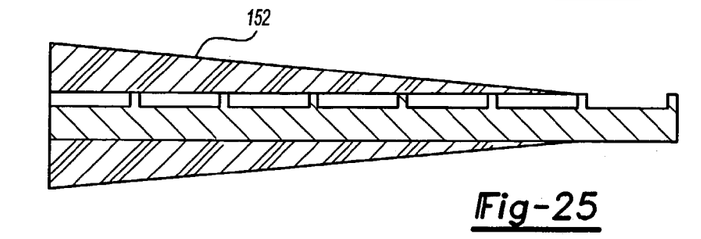
Figure 26:
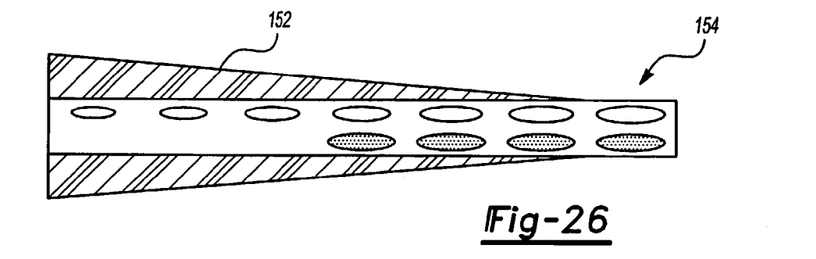

To illustrate, FIG. 25 shows an embodiment that has a smooth sloping barrier layer 152. As seen in FIG. 26, a suitable pattern 154 of wells for the pharmaceutical agent may be employed if desired such as described previously. The pattern may be selected as desired.

Figure 27:
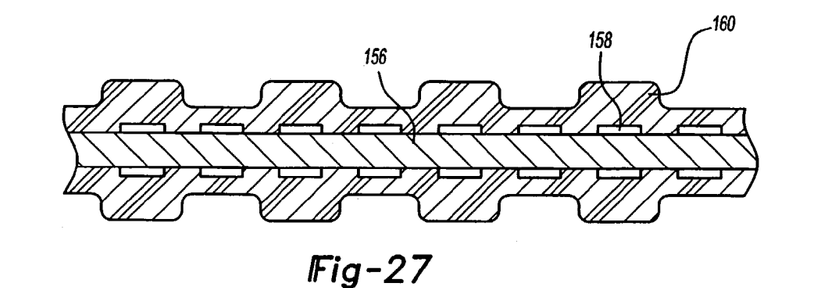

FIG. 27 illustrates yet another alternative in which an implant member 156 is generally smooth over its outer surface. Pharmaceutical agent is applied to define raised regions 158 over which a barrier layer 160 is applied. The thickness of the barrier layer may vary along the length so that as the thickness diminishes over time, only certain regions 158 will become exposed. Thus it is possible that there can be simultaneous exposures of pharmaceutical agent along substantial portions of, if not the entirety of the length of the implant.

Figure 28:
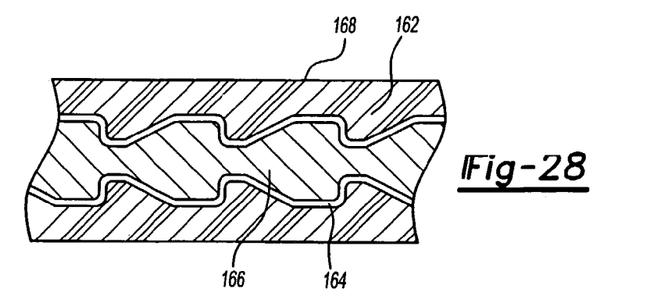

FIG. 28 illustrates another strategy for helping to facilitate simultaneous exposure along the length of an implant. As in FIG. 27, a barrier layer 162 overlies layer of pharmaceutical agent 164 on an implant member 166 (e.g., having a contoured surface), which though possibly irregular is illustrated with a smooth surface 168, substantially free of a slope.

While a preferred method and device herein contemplates an opthalmological implant placed in an eye following cataract surgery, other applications are also possible. For example, one approach may be to provide an implantable tube that has a biodegradeable or bio-erodable material on the inside of the tube. Over time the tube inner diameter will gradually increase. In this manner, such a tube can be placed in a passageway between the globe and the subconjunctival space outside the scleral wall of the eye during a glaucoma surgery, for helping to regulate pressure by way of the gradually changing tube inner diameter.

The present invention also finds utility in other biomedical implant applications. For example, it is possible to employ the techniques herein for preparing a coated stent having a sustained release pharmaceutical agent on it, on a suture material, on a surgical instrument, a breathing tube, an othopedic pin, a syringe needle, an intravenous needle, or otherwise.

It is also contemplated that a post of body piercing jewelry article can be coated with a sustained release composition that releases on anti-inflammatory, an antibiotic, steroid, or other pharmaceutical agent. A like approach may be taken for treating animal tagging devices prior to tagging an animal (e.g., a livestock tag). In this manner, infection or other adverse reactions can be treated when making an initial piercing.

It will be readily appreciated that for preparing devices other than opthalmological implants, the methods herein described can be adapted readily by selecting suitably desired materials and agents, and by substituting the implant members described herein with the desired article to be coated (e.g., a stent, an earring post, livestock tag post, etc.).

In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for making an endocapsular tension ring comprising the steps of:
   a. providing a biocompatible filament that includes at least one crevice for holding a pharmaceutical agent selected from the group consisting of an antimicrobial, an antithrombotic, an antiseptic, an antifungal, a chelating agent, an anticoagulant, an antibiotic, an anti-inflammatory, a steroid, an antiglaucomatous, and a combination thereof, the filament being configured for insertion into an eye as an endocapsular tension ring;
   b. attaching a first layer including the pharmaceutical agent to the filament so the pharmaceutical agent is within the at least one crevice; and
   c. attaching a sustained release medium barrier layer including a varying thickness along the length of the filament over the first layer, the barrier layer including a material selected from a bioerodible material, a biodegradable material, a bioavailable material or a mixture thereof, and the varying thickness of the barrier layer along the length of the filament permitting release of the pharmaceutical agent at different positions along the filament at different times.

2. The method of claim 1, wherein the endocapsular tension ring is fabricated from polymethylmethacrylate.

3. The method of claim 2, wherein the outer surface of the endocapsular tension ring, having the sustained release medium and the pharmaceutical agent applied thereto, includes a tapered surface.

4. The method of claim 3, wherein the pharmaceutical agent is applied to the endocapsular tension ring along the length of the endocapsular tension ring as an intermittent layer.

* * * * *

UNITED STATES PATENT AND TRADEMARK OFFICE
CERTIFICATE OF CORRECTION

PATENT NO. : 7,090,888 B2 Page 1 of 1
APPLICATION NO. : 10/346671
DATED : August 15, 2006
INVENTOR(S) : Michael E. Snyder and Eric M. Dobrusin It is certified that error appears in the above-identified patent and that said Letters Patent is hereby corrected as shown below:

Title page, item 57 Abstract
replace "bloavailable"
with --bioavailable--.

Signed and Sealed this

Twenty-fifth Day of March, 2008

JON W. DUDAS
*Director of the United States Patent and Trademark Office*